(12) United States Patent
Green et al.

(10) Patent No.: US 6,180,060 B1
(45) Date of Patent: ***Jan. 30, 2001

(54) ANALYZER TRANSPORT DEVICE

(75) Inventors: Thomas B. Green, Forest Park; Robert G. Westendorf, Cincinnati, both of OH (US)

(73) Assignee: Tekmar Corporation, Cincinnati, OH (US)

( * ) Notice: Under 35 U.S.C. 154(b), the term of this patent shall be extended for 0 days.

This patent is subject to a terminal disclaimer.

(21) Appl. No.: 08/401,876

(22) Filed: Mar. 10, 1995

Related U.S. Application Data

(62) Division of application No. 08/185,649, filed on Nov. 30, 1993, which is a division of application No. 08/149,716, filed on Nov. 9, 1993, which is a continuation of application No. 07/969,415, filed on Oct. 30, 1992, now abandoned, which is a division of application No. 07/487,583, filed on Mar. 2, 1990, now abandoned, said application No. 08/185,649, is a continuation of application No. 08/009,342, filed on Jan. 26, 1993, now abandoned, which is a continuation of application No. 07/487,583, filed on Mar. 2, 1990, now abandoned.

(51) Int. Cl.$^7$ .................................................. G01N 30/02
(52) U.S. Cl. .................. 422/64; 73/863.01; 73/863.11; 73/864.87; 73/23.41; 366/108; 422/67; 422/70; 422/68.1; 422/99
(58) Field of Search .................. 73/19.1, 23.41, 73/23.42, 863.01, 863.11, 863.12, 863.61, 864.21, 864.23, 864.85, 864.87; 366/108, 110–112, 145, 146, 208, 209, 218, 240; 422/62–64, 67, 68.1, 70, 75, 89, 90, 99, 102; 436/47, 48, 161, 174, 172, 181

(56) References Cited

U.S. PATENT DOCUMENTS 3,418,080  12/1968  Rochte et al. ..................... 422/81
3,479,880  11/1969  Mutter et al. ..................... 73/863
3,508,442   4/1970  Lightner et al. .................. 73/864
3,545,279  12/1970  Jentzsch et al. .............. 73/865.85 X
3,549,330  12/1970  Jungner et al. ................... 422/64 X
3,581,574   6/1971  Smith ........................... 73/864.23
3,631,724   1/1972  Oster et al. .................... 73/864.13

(List continued on next page.)

FOREIGN PATENT DOCUMENTS 1297904   6/1969  (DE) .
0071092   2/1983  (EP) .
1367431   9/1974  (GB) .
1435374   5/1976  (GB) .
2069974   9/1981  (GB) .
2130367 * 5/1989  (GB) .
56-54356  5/1981  (JP) .
58-80555  5/1983  (JP) .
2-91564   3/1990  (JP) .
8912829  12/1989  (WO) .

OTHER PUBLICATIONS

P. Gagliardi et al. *Chem. Abstr.* 1981, 95, 72747h.
R. Otson *Anal. Chem.* 1981, 53, 929–931.
F. McAuley et al. *J. Anal. Toxic.* 1983, 7, 213–215.
Z. Penton *Clin. Chem.* 1985, 31, 439–441.
F. Poy et al. *J. Chromatog. Sci.* 1985, 23, 114–119.
G.P. Robertson et al. *Plant Soil* 1985, 83, 453–457.

(List continued on next page.)

*Primary Examiner*—Arlen Soderquist
(74) *Attorney, Agent, or Firm*—Westerman, Champlin & Kelly, P.A.

(57) ABSTRACT

A sample transport device for use in analyzing samples by the headspace analysis technique. The device has a cylindrical platen with counterbored chambers for accepting sample vials. The platen is heated and caused to rotate from a first vial transport point to a sampling point and then back for ejection of the sample vial. Vertical movement of the sample vials is accomplished by use of elevator rods connected to level winding screws mounted below the cylindrical platen.

24 Claims, 4 Drawing Sheets

U.S. PATENT DOCUMENTS

| | | | |
|---|---|---|---|
| 3,754,443 | 8/1973 | Harris, Sr. et al. ..................... | 73/863 |
| 3,832,135 * | 8/1974 | Drozdowski et al. ............. | 422/65 X |
| 3,832,140 | 8/1974 | Lorch et al. ............................ | 422/65 |
| 3,849,070 | 11/1974 | Garza et al. ......................... | 436/133 |
| 3,897,216 * | 7/1975 | Jones .................................. | 422/65 X |
| 3,954,012 | 5/1976 | Christen et al. ....................... | 73/864 |
| 4,199,988 | 4/1980 | Riegger .......................... | 73/864.85 X |
| 4,237,733 | 12/1980 | Kolb et al. .................... | 73/864.23 X |
| 4,294,126 | 10/1981 | Tomoff et al. ..................... | 422/64 X |
| 4,335,620 | 6/1982 | Adams .............................. | 422/64 X |
| 4,458,544 | 7/1984 | Gyer et al. ............................ | 422/67 |
| 4,464,940 | 8/1984 | Pospisil ............................ | 73/864.21 |
| 4,476,733 | 10/1984 | Chlosta et al. ..................... | 422/63 X |
| 4,478,095 | 10/1984 | Bradley et al. ..................... | 422/64 X |
| 4,713,974 | 12/1987 | Stone ................................. | 422/64 X |
| 4,848,917 | 7/1989 | Benin et al. ........................... | 422/99 |
| 4,944,781 | 7/1990 | Ruggirello et al. .................... | 55/386 |
| 4,974,460 | 12/1990 | Baxter ............................... | 422/102 X |
| 5,050,425 | 9/1991 | Robbins ................................ | 73/19.1 |
| 5,116,578 | 5/1992 | Baxter ................................ | 422/64 X |
| 5,171,530 | 12/1992 | Pennatto ................................ | 422/63 |

OTHER PUBLICATIONS

R. Hiltunen et al. *Proc. Int. Symp. Essential Oils Arom. Plants* 1985, 23–40.

R. Miller et al. *Proc. Int. Symp. Capil. Chromatog.* 1981 267–293.

L.A. Pranto–Soetardhi et al. *J. Int. Environ. Anal. Chem.* 1986, 25, 151–159.

R. Gard et al. *Chem. Abstr.* 1987, 106, 187975U.

G.P. Robertson et al. *Chem. Abstr.* 1985, 102, 184208C.

L.A. Pranoto–Soetardin et al. *Chem. Abstr.* 1986, 105, 96131d.

Y. Yamano et al. *Jpn.J. Ind. Health* 1987, 29, 196–201.

G. Picard et al. *Can. Inst. Food Technol. J.* 1971, 4, 112–115.

N. Hamamura et al. *Eisei Kagaku* 1976, 22, 323–325.

M. Umino et al. *Toyo Soda Kenkyu Hokoku* 1977, 21, 83–88.

M. Sakata et al. *J. Toxical. Sci.* 1980, 5, 35–43.

M. Jakubowski, et al. *Bromat. Chem. Toksykol.* 1980, 13, 263–270.

H. Radzikowska–Kintzi et al. *Int. Arch. Occup. Environ. Health* 1981, 49, 115–123.

S. Miyaura et al. *Eisei Kagaku* 1983, 29, 83–90.

S. Miyaura et al. *Eisei Kagaku* 1985, 31, 87–94.

T. J. Wisk et al. *J. Am. Soc. Brew. Chem.* 1986, 44, 72–77.

H. Tsuchihashi et al. *Forens. Sci. Int.* 1990, 45, 181–189.

D. Leggett *Report* 1979 CRREL–SR–79–24.

Perkin–Elmer Brochure "Head Space Sampler HS=6".

* cited by examiner

ANALYZER TRANSPORT DEVICE

This is a divisional application of copending application Ser. No. 08/185,649 filed Nov. 30, 1993 which is a continuation of Ser. No. 08/009,342 filed Jan. 26, 1993 now abandoned which is a continuation of Ser. No. 07/487,583 filed Mar. 2, 1990, now abandoned, and a division of copending application Ser. No. 08/149,716 filed Nov. 9, 1993, which is a continuation of Ser. No. 07/969,415, filed on Oct. 30, 1992, now abandoned, which in turn is a division of application Ser. No. 07/487,583, filed Mar. 2, 1990, now abandoned.

FIELD OF THE INVENTION

The invention relates to devices for transporting large numbers of samples to a sampling site preparatory to analysis of those samples.

BACKGROUND OF THE INVENTION

Head space analysis techniques are employed to analyze for volatile components in largely non-volatile mixtures. For example, this analytical technique is used in determining the amount of alcohol in a known quantity of blood. The technique is also used for analyses of volatile components in other body fluids. Further applications include analysis of trace organic compounds in water samples, testing for the presence of solvents in drugs, for solvents or monomers in polymers, for fragrances in toiletries, for flavors or aromas in foods, and the like. It is desirable in these applications to have a transport device capable of transporting samples automatically at high rates to the analyzing instrument. It is also desirable for the transport device to be able to be programmed to automatically repeat the sampling of one or more vials one or a number of times. This feature is useful for improving the precision of the analysis.

The amount of volatile components in the gaseous headspace portion over a liquid sample in a closed vial is known to vary with the temperature of the liquid sample. Therefore, it is very important to maintain the temperature of the liquid sample within a very narrow range in the transport prior to analysis. Further, because the actual quantity of material in the headspace over a liquid sample is very small, any contamination from outside sources would substantially alter the analysis of the headspace gases. Therefore, the risk of outside contamination must be minimized during the sampling process. Also, because sample vials are made in various sizes, it is desirable that the transport device be able to accommodate different sizes.

SUMMARY OF THE INVENTION

It is therefore an object of the invention to provide a transport device which is readily automated and capable of running large numbers of individual samples.

It is another object of the invention to provide a transport device capable of accurately regulating the temperature of samples stored therein.

It is yet another object of the invention to provide a transport device capable of performing repeated analyses on a single group of samples.

It is yet a further object of the invention to provide a transport device capable of accepting and sampling vials of different sizes.

Further objects and advantages of the invention will become evident from the description which follows.

The invention relates to a sample vial transport device having a rotatable heated platen with a plurality of chambers to hold sample vials. The sample vials are loaded into the chambers by a vial transport which conveys the sample vials from a point above the individual chamber. The platen therefore does not have to move axially to input a vial or to sample the vial contents, as discussed below. This significantly reduces the complexity of the vial transport mechanism. Vials from which samples have already been taken are ejected from the individual chamber by reversing the operation of the vial, trainsport.

Sampling of the contents of the sample vial is done at a point removed from the vial inlet point. The sample vial is rotated toward the sampling point, at which time the sample vial is brought into contact with a needle by mating means. The needle extracts at least a portion of the contents of the vial for sampling by puncturing a septum in the cap of the vial.

The platen is preferably heated electrically. Electrical heating is preferred over oil bath heating, which tends to introduce trace materials attributable to the oil into the analysis instrument and thereby alter the analysis results. Further, oil vapors condense on mechanisms and hold dirt. The oil baths need to be constantly stirred to maintain temperature uniformity, and they pose a greater safety hazard to the operator.

The vial from which a sample has been extracted then continues back to the inlet point within the chamber. At that time, it is either ejected from the platen by the vial transport or alternatively remains in the chamber for an additional rotation and sampling operation. The transport device chambers are also capable of holding liner sleeves, or inserts, which permit sampling of different size vials. Typically, the vials utilized have volumes of 5 ml, 10 ml or 20 ml.

In the preferred embodiment of the invention, the needle is stationary and positioned above the platen and a second vial transport is utilized as the mating means to push the sample vial upward from the bottom of the chamber to cause puncturing of the septum with the needle. However, the needle can be movable to puncture the septum as an alternative embodiment.

The rate of transport of gaseous components from the liquid to the headspace of the vial is a function of the mean path length the components must travel through the liquid to reach the headspace. It has been found that mixing the vial contents dramatically reduces the mean path length and thus improves the transport rate. To facilitate the mixing, the invention includes a mixing device having a vertically displaceable rod positioned below the platen which rises through the bottom of the platen to contact the sample vial bottom in a chamber between the inlet point and the sampling point. The rod is preferably connected to a DC solenoid which is repeatedly energized for short periods to cause the rod to pulse and thereby shake the sample vial in an up and down motion within the chamber. This mixing motion aids in equilibrating the concentration of the material to be analyzed in both the liquid and gas phases within the sample vial.

Further objects, advantages and features of the invention will become apparent upon review of the detailed description of the invention and the drawings in which:

DETAILED DESCRIPTION OF THE INVENTION

The invention in its broader aspects relates to a transport device for conveying sample vials to a sampling location for effecting withdrawal of at least a portion of the vial contents for analysis thereof, comprising a platen which is rotatable around a central axis having a plurality of counterbored chambers, a heater for the platen, a first vial transport which operates to convey a vial into a chamber from a point above the chamber and the reverse, a needle for extracting at least a portion of the vial contents from the vial, and mating means for bringing the needle into contact with the vial contents to allow extraction thereof.

Figure 1:
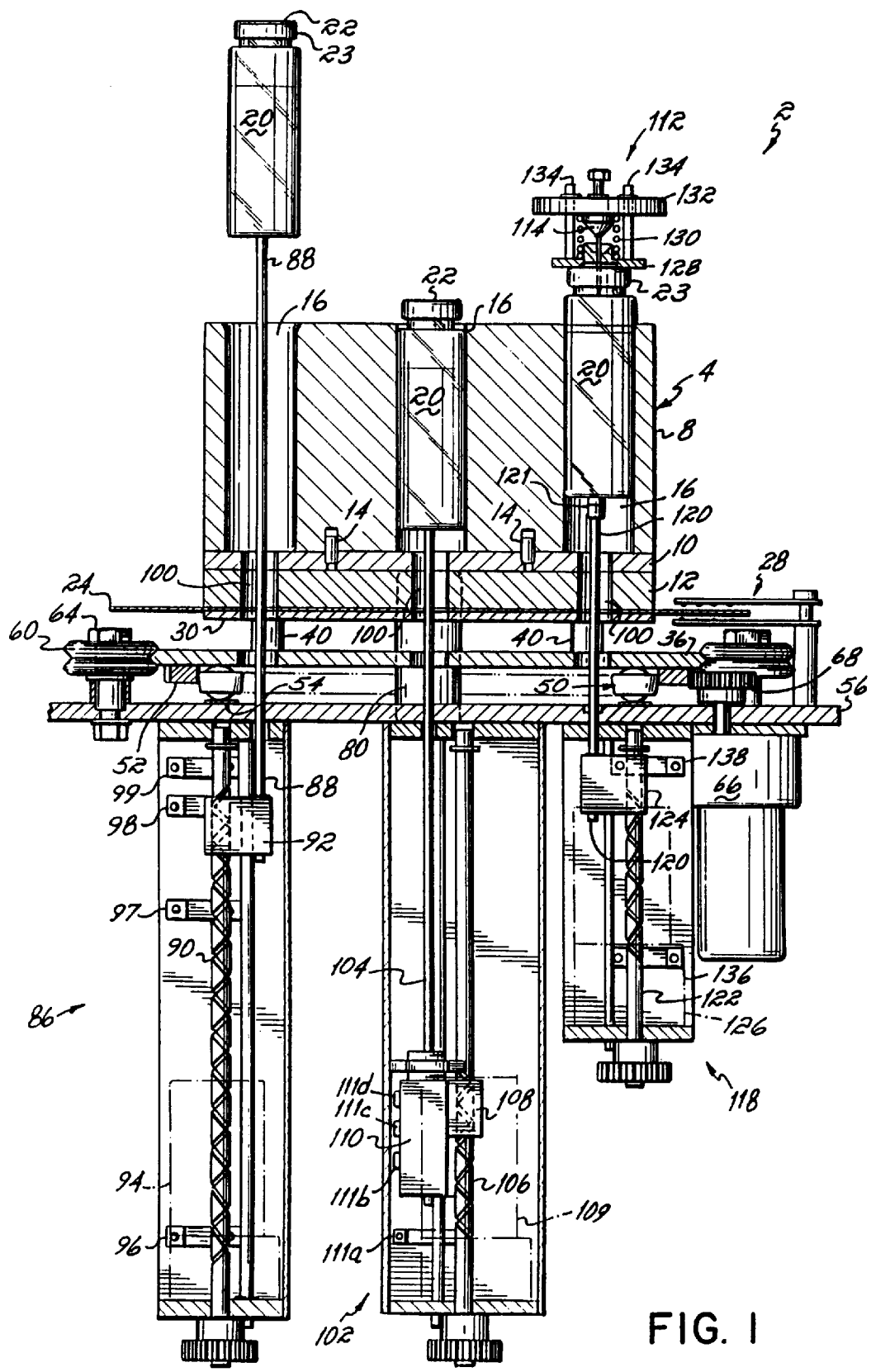
FIG. 1 is a side view of the transport device, taken in an axial cross sectional view through the unit with certain features out of position to aid in understanding the invention.

In referring to the drawings, FIG. 1 shows the sample transport 2 having a platen 4. The platen 4 is a cylindrical block made of heat-conducting material, preferably aluminum, which is manufactured preferably by combining the throughbored block 8 with the bored plate 10 and insulation plate 12. The throughbored holes in block 8 run axially through the block and are positioned near the periphery of the block. These holes mate with the bored holes in plate 10, the holes having a smaller diameter than those in block 8. Mating is facilitated by the use of dowel pins 14 in the bored plate 10 which key into mating holes in the block 8. The mating of throughbored block 8 with bored plate 10 creates individual chambers 16 for holding a sample vial 20 having a septum 22 within cap 23. Alternatively, a single block can be counterbored to form the same chambers as are created by combining block 8 with plate 10. However, the preferred embodiment is easier to manufacture and therefore of lower cost.

Figure 4:
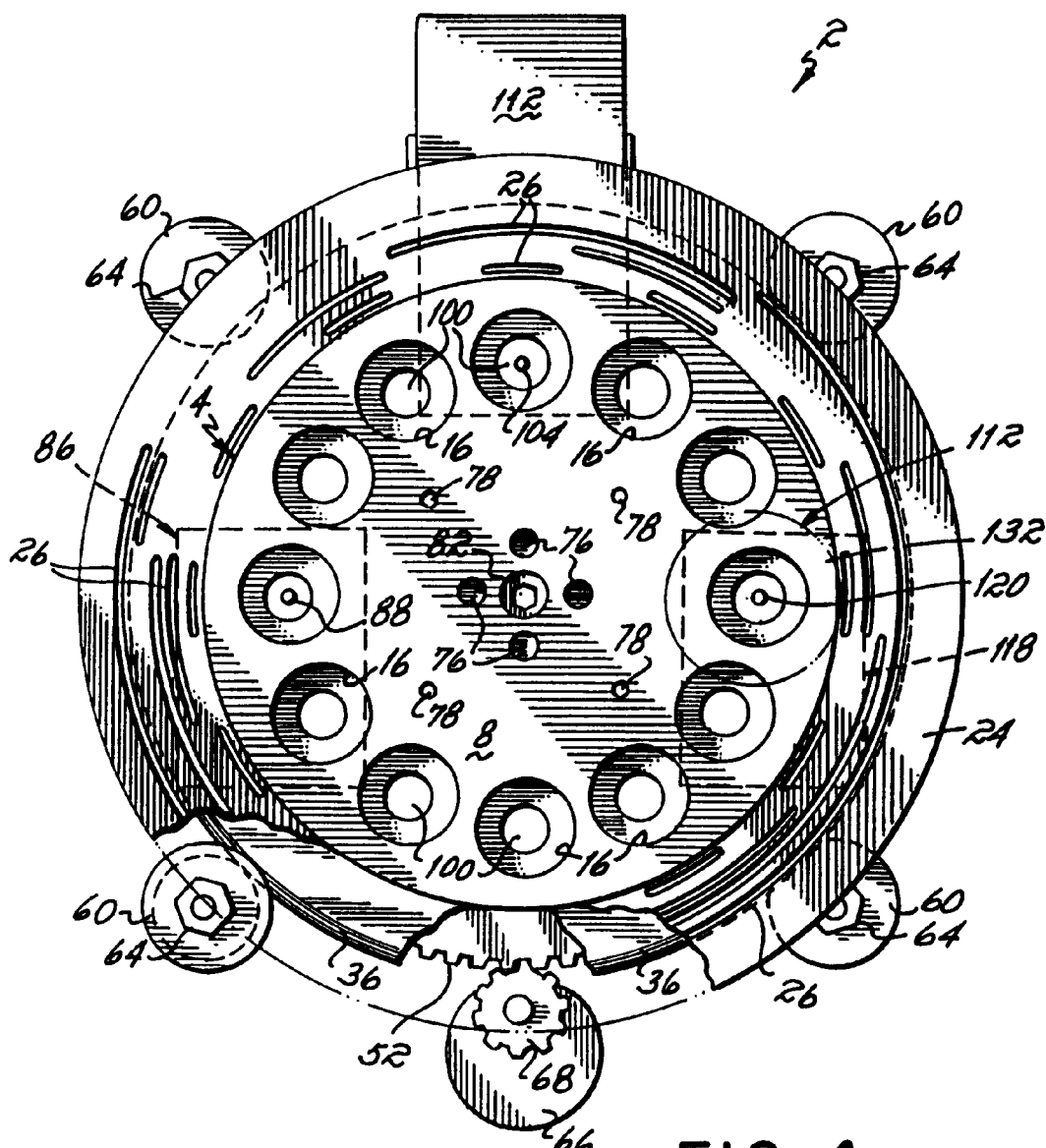
FIG. 4 is a top view of the transport device.

Below insulation plate 12 is positioned an encoder wheel 24. This wheel has a series of slots 26, an example of which are shown in FIG. 4, which are read by a photodiode transmissive switch assembly 28 to thereby provide a means both for determining the position of the platen 4 and for centering the chambers 16 over the various mechanisms, to be described in detail below. The transmissive switch 28 has a light generating element and a light detecting element, and the encoder wheel rotates between these two elements. Position is determined by the number and location on the encoder wheel 24 of slots passing light through to the detecting element at any one time. Below the encoder wheel 24 is a support plate 30. Plate 12 is preferably manufactured from a machineable glass fiber, one example of which is known as MARINITE I. MARINITE I, manufactured by Johns-Manville Corp., Denver, Colo. is comprised of calcium silicate with inert filters and reinforcing agents. Alternatively, other materials meeting the requirements of machineability and heat insulative ability may be used. For purposes of discussion, the platen 4 will include the throughbored block 8, bored plate 10 insulation plate 12 and support plate 30. The insulation plate 12, support plate 30 and the encoder wheel 24 are bored to match the borings in plate 10.

Figure 2:
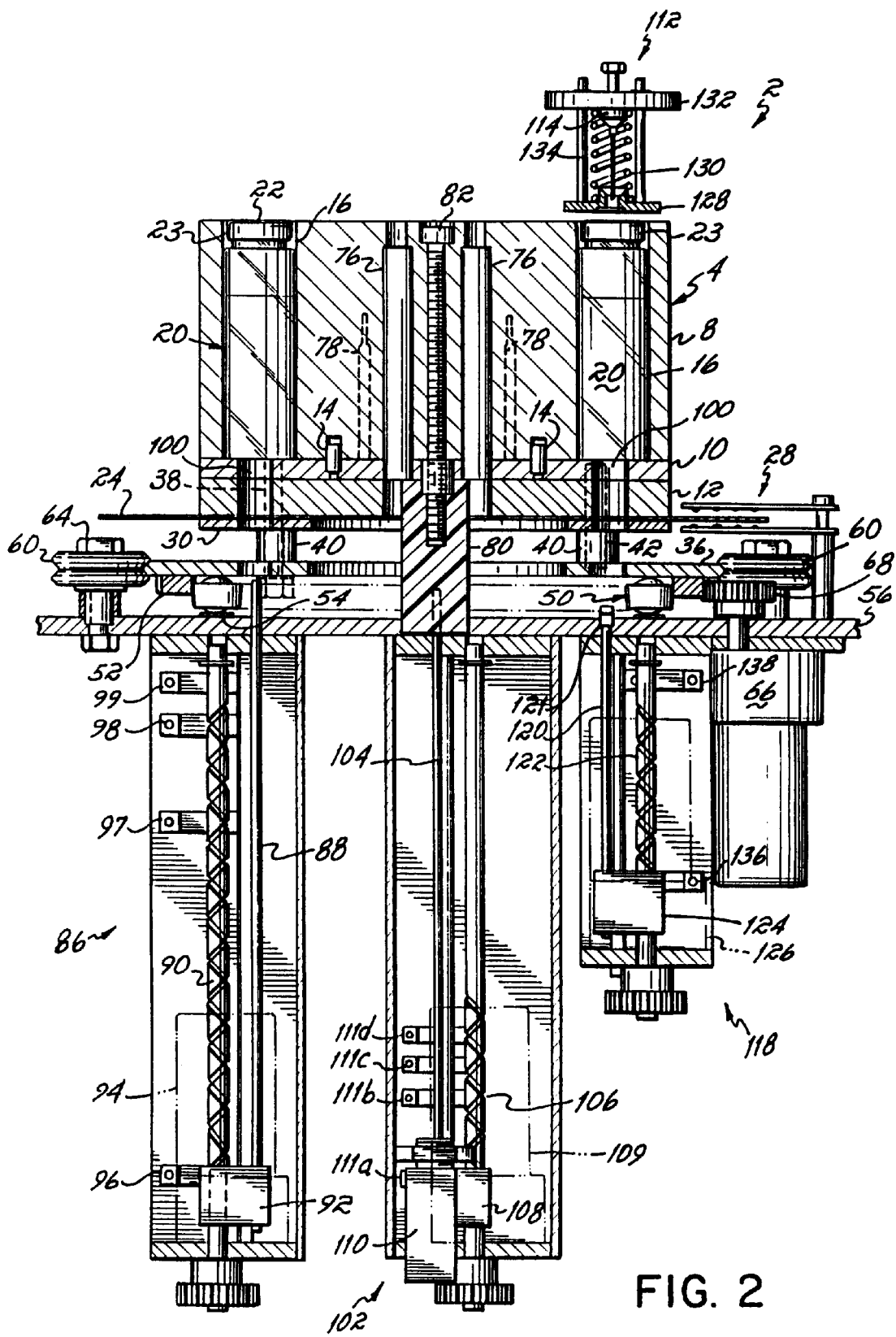
FIG. 2 is a side view of the device, taken with a different cross section, and showing all elevator rods in the retracted position.

The platen 4 with encoder wheel 24 is secured to the guide track 36 through screws 38 and spacers 40, several of which being depicted in FIGS. 1 and 2. Mating is facilitated by matching dowel pins 42 (only one shown) with mating holes in bored plate 10, insulation plate 12, encoder wheel 24 and support plate 30. The guide track 36 in turn is supported on a ball bearing cage assembly 50. The cage assembly 50 is retained in position below the guide track 36 by the inside shoulder of platen gear 52, which is secured to the bottom side of guide track 36. The bearings comprising the ball bearing cage assembly 50 rest on a thrust washer 54, made preferably from hardened tool steel, which is positioned onto the base plate 56 and maintained in position by pins (not shown) driven into the base plate 56 adjacent the outside diameter of the thrust washer 54. Alternatively, a channel corresponding to the diameter and thickness of the thrust washer 54 could be cut into the base plate 56 and the washer positioned therein. However, this operation requires additional machining and is not necessary to the effective operation of the sample transport.

The guide track 36, and therefore the platen 4, is caused to align properly around a single axis during rotation by the presence of roller wheels 60 mounted onto the base plate 56 by bolt and sleeve assemblies 64. The roller wheel 60 mates with the edge of the guide track 36 along its periphery to maintain the proper orientation. The platen 4 is caused to rotate by actuation of drive motor 66 having a drive gear 68 attached thereto which cooperates with the teeth on platen gear 52.

The throughbored block 8 and bored plate 10 are heated preferably by cartridge heaters 76. The temperature of the block 8 and bored plate 10 is measured by temperature measurement probes 78. These probes preferably are thermocouples, but may be resistance temperature devices or other like device. The cartridge heaters 76 may be easily removed for servicing by removal of an epoxy plug 80 secured to the platen 4 by platen-bolt 82, which is shown in FIG. 2.

Sample vials 20 are lowered into the platen 4 and ejected therefrom by a first vial transport 86 consisting of an elevator rod 88 connected to a level winding screw 90 by screw follower 92. The elevator rod 88 is displaced vertically by rotating level winding screw 90 through use of transport motor 94. The elevator rod 88 contacts the bottom of sample vial 20 by travelling upward through aperture 100, which is of smaller diameter than chamber 16. The aperture 100 is bored through bored plate 10, insulation plate 12, encoder wheel 24 and support plate 30. The extent of travel of the elevator rod 88 is regulated by lower limit switch 96 and upper limit switches 97, 98 and 99. Switch 97 stops the upward travel of the elevator rod 88 when the sample vial is to be manually loaded or unloaded. When the vials are to be automatically loaded and unloaded, switches 98 and 99 are used. Switch 98 stops the elevator rod 88 at the auto load point, and switch 99 is for the auto unload, or eject, point.

The sample vial 20 shown in the center chamber position in FIG. 1 is mixed by the mixer device 102, consisting of an elevator rod 104 which rises vertically through aperture 100 by rotation of level winding screw 106 connected to the elevator rod 104 by screw follower 108. Rotation is effected by actuation of mixer motor 109. The DC solenoid 110 located on the screw follower 108 and connected to the elevator rod 104 pulses the rod to provide the necessary mixing. The solenoid 111 is supplied with a variable voltage input which varies the power supplied to the elevator rod 104. The higher the power, the further the vial 20 rises in the chamber 16 in response to the pulse. This variable voltage feature allows varying of the intensity of mixing.

As discussed above, the transport device 2 as presently configured is capable of accepting vials of 5, 10 and 20 ml volumes. The figures show the 20 ml vials. The smaller vials require liner sleeves, or inserts (not shown), which support the cap 23 and maintain the septum 22 uniformly near the top of the throughbored block 8. The inserts also have a hole in the bottom through which the elevator rods 104 and 88 travel. Because the caps of the different-sized vials will all be at approximately the same height in the chamber 16, it follows that the bottoms of the vials will rest different distances above the bottom of the chamber 16. During mixing, the elevator rod 104 raises the vial only about 1/16 inch above a rest position. Therefore, with different size vials, the elevator rod 104 must rise different lengths to contact and mix the vials. The limit switches 111a, b, c, d indicate the elevator rod 104 rest position, and mixing points for the 20 ml, 10 ml and 5 ml vials, respectively.

The sample vial 20 in the right chamber is shown in FIG. 1 to be proximate to the needle assembly 112 and is in position for sampling. The vial 20 is raised from a rest position to puncturing contact of the septum 22 with needle 114 by a second vial transport 118, which serves as the mating means to bring the needle into contact with the vial contents. The second vial transport consists of an elevator rod 120 terminating with a rod tip 121 which is raised vertically to contact the bottom of the sample vial 20 (or insert supporting a sample vial) by rotation of level winding screw 122 connected to the elevator rod 120 by screw follower 124. The rod tip has a larger diameter than the hole bored into the bottom of a vial insert to raise the combination of vial and insert. Where the 20 ml vial is used, the rod tip 121 contacts the bottom of vial 20 directly. Rotation of the level winding screw is effected by actuating transport motor 126. After sampling is completed, the sample vial 20 is returned into the chamber 16 by reverse movement of the elevator rod 120. The septum 22 is freed from needle 114 with the assistance of a wiper plate 128 which pushes against the sample vial cap 23 via spring 130 loaded against needle flange 132. The wiper plate 128 is maintained in position relative to the needle 114 by means of guide rods 134. The extent of travel of the elevator rod 120 is regulated by lower limit switch 136 and upper limit switch 138.

FIG. 2 shows the sample transport 2 with all elevator rods in the fully retracted position. It can be seen that the needle 114 is positioned directly above the platen 4. The close positioning of the needle assembly 112 to the top of the platen 4 permits the sample vials 20 to be sampled while only being lifted a short distance inside the chamber. This close arrangement of needle assembly 112 to the top of the platen 4 minimizes temperature fluctuation within the individual sample vials as the sample is withdrawn.

The various components of the platen are secured to each other and to the epoxy plug 80 by the platen bolt 82.

FIG. 4 shows the top view of the transport device and the relationship of the components. The platen 4 has positioned near its outside circumference a plurality of chambers 16. Inside the circumference of the chambers are located the temperature measurement probes 78. Near the axis of the platen 4 are the cartridge heaters 76. The various components comprising the platen 4 are secured by the platen bolt 82. Below the platen 4 at the nine o'clock position is the first vial transport 86. The tip of the elevator rod 88 can be seen in position ready to rise through aperture 100. At the twelve o'clock position below the platen 4 is the mixer device 102, with the tip of elevator rod 104 appearing in aperture 100. At the three o'clock position below the platen is located the second vial transport 118, with the tip of elevator rod 20 showing. In phantom is depicted the needle flange 132 which is located over the chamber corresponding to the second vial transport 118.

Figure 3:
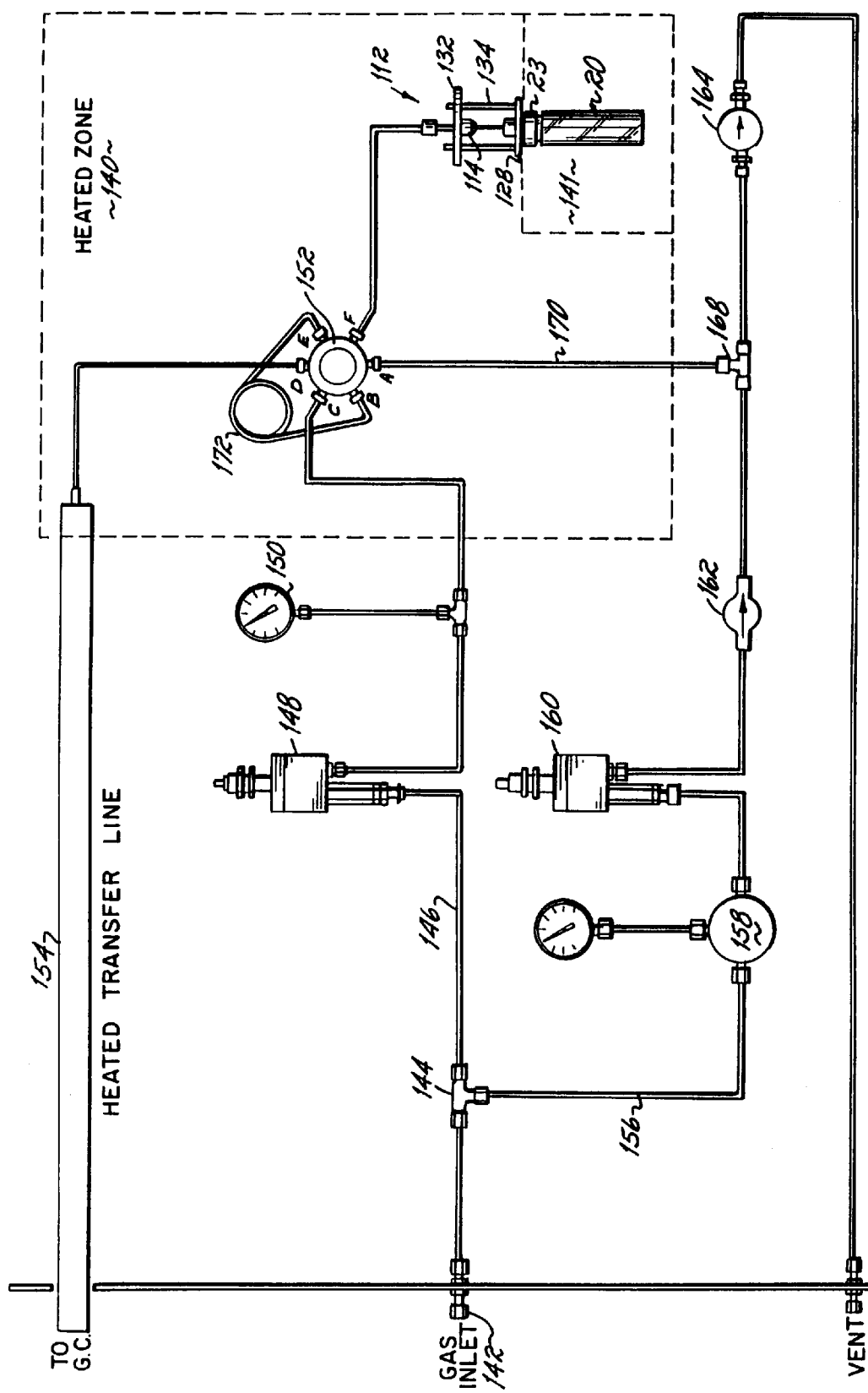
FIG. 3 is a schematic of the carrier gas and sample flow patterns.

The sampling of the headspace contents operates as follows. The headspace contents within a sample vial 20 are removed from the sample vial 20 and conducted to a gas chromatograph (G.C.) for analysis by the following procedure. FIG. 3 is a schematic showing the gas flow pattern into the sample transport, depicted in part as the heated zone 140 and separate platen heated zone 141, out the sample transport and then to the gas chromatograph. Zone 141 is the platen 4 itself. The heating of this zone 141 has been generally discussed and will be described in more detail below. The zone 140 is heated to prevent condensation in the lines between the needle 114 and the gas chromatograph. The temperature in this zone is typically set about 10° to about 25° C. higher than the platen 4 temperature.

Carrier gas, typically helium, enters gas inlet 142 from a tank controlled with a pressure regulator (not shown). The gas supply is split at T-connection 144. The tubing and connections through which the carrier gas flows are made from nickel alloy, copper, stainless steel, or other material which does not evolve any compounds which might affect the G.C. analysis and which is not permeable to compounds in the air which might diffuse through-the material and be carried to the G.C. Carrier gas flows through first line 146 at a pressure set at the tank regulator, typically about 60 psi, to a gas chromatograph flow controller 148. The controller 148 is connected in line to pressure gauge 150. Carrier gas then flows into six port valve 152 having ports A, B, C, D, E and F. The carrier gas flowing through the first line 146 ultimately enters six port valve 152 at port C, exits through port D and continues through the heated transfer line 154 into the gas chromatograph. This flow of gas is always on to constantly purge the gas chromatograph.

The remaining flow of carrier gas after splitting passes through second line 156. The carrier gas flowing through this second line is used to purge the needle 114 and to pressurize the sample vial 20 after the septum 22 has been punctured by needle 114. Pressure is adjusted by regulator 158 within a range of about 5 to about 30 psi, depending on the application. The flow is regulated by flow controller 160. Carrier gas flow through the needle 114 is turned on and off by a solenoid operated pressurization valve 162. The flow controller 160 is set at a level sufficient to pressurize the sample vial in a reasonable time, but not so high as to waste excessive amounts of carrier gas as the needle is being purged. Typically, the valve 162 is open to constantly purge the needle 114. With the pressurization valve 162 on, and vent valve 164 off, carrier gas flows through T-connection 168 to inlet line 170 and then into the six port valve 152 at port A. The carrier gas flows from port A into port B, through sample loop 172, into port E, out port F and through the needle 114 into the sample vial 20. After a programmed amount of time sufficient to pressurize the vial 20 to at least the same pressure as that set at the regulator 158; the pressurization valve 162 is turned off and the pressure within the lines from that valve to the sample vial is allowed to equilibrate.

After a preprogrammed equilibration time of several seconds to several minutes, the vent valve 164 is opened to allow the vial gases, consisting of carrier gas and headspace contents, to vent. Carrier gas with the headspace contents flows back through needle 114, into the six port valve at port F and into the sample loop 172 and out port A toward the vent valve 164. After an additional programmed time, the vent valve 164 is closed and the six port valve 152 is cycled. The carrier gas in the first line 146, which remained on and flowed out port D to the gas chromatograph, is now caused to flow through port C to port B after the cycling. The carrier gas flows into the sample loop 172 and flushes the contents into port E which is now connected with port D. This allows the materials to flow into the gas chromatograph through heated transfer line 154. After the sample contents have been injected into the gas chromatograph, the six port valve 152 returns to its home position, the sample vial 20 is removed from needle 114 and the pressurization valve 162 is again opened to purge the needle of any residual headspace material. When a new sample vial 20 is brought in contact with the needle, the procedure repeats.

The analyzer transport device described above is used preferably for preparing samples for analysis using the headspace analysis technique, wherein the gaseous sample is heated to a set temperature and the contents sent to a gas chromatograph. The operable temperature range is typically room temperature plus 10° C. to about 200° C. The above transport device can be automatically loaded and unloaded, and large numbers of samples can be processed without constant operator supervision. The electrically powered functions of the device are controlled through a keypad or other similar type of control unit (not shown) which, among other functions, adjusts the sample vial processing rate through the transport device, adjusts temperature, severity and time of mixing, sampling order by use of the encoder wheel in combination with the photodiode transmissive switch assembly, and number of repetitions of analysis of the headspace contents of a single sample vial.

Thus it is apparent that there has been provided in accordance with the invention, a sample transport device that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A device for heating and agitating sample vials having caps with a septum therein for withdrawing gaseous material from a headspace of said vials for analysis by gas chromatography, comprising:

a platen mounted on a support and having a plurality of chambers, each of said chambers having a bottom wall for supporting one of said sample vials on the bottom wall, the bottom wall having an opening for providing access to retained sample vials from below;

an electrically powered heater mounted to heat said platen;

a vial transport mounted relative to the platen for transporting a vial from above a chamber to lower the vial into such chamber, and the reverse;

a vial mixing device mounted relative to the platen and alienable with the chamber and comprising a rod at least partially extendible into said chamber through said opening from below to contact said vial and mix the contents by pulsating the vial to increase the rate of transport of gaseous components from liquid in said sample vial to said headspace; and a needle mounted relative to the platen for alignment with the chamber for extracting material from said headspace through said septum after said needle punctures said septum of said vial.

2. The device of claim 1, wherein each of said chambers is sized to slideably receive one of said sample vials and hold it in heat conductive relation to the platen.

3. The device of claim 2, wherein the vial mixing device in pulsating the vial causes the vial to move up and down within the chamber to maintain the vial in heat conductive relation to the platen.

4. The device of claim 1, wherein the platen comprises heat-conducting material.

5. The device of claim 4, wherein the platen comprises aluminum.

6. The device of claim 1, wherein a tip of said rod extends into said chamber through said opening from below to contact said vial.

7. The device of claim 1, wherein the electrically powered heater comprises a cartridge heater.

8. The device of claim 1, wherein said rod is selectively at least partially extendible into each of said plurality of chambers.

9. A transport device for handling sample vials having caps with a septum therein for withdrawing material from a headspace of said vials for analysis by gas chromatography, comprising;

a platen having a plurality of side by side chambers, said chambers having bottoms for retaining said sample vials above said bottoms, and the bottoms providing an access opening to retained sample vials from below;

an electrically powered heater located within said platen;

a vial transport which conveys a vial into one of said chambers from a point above said chamber to rest on the bottom of the chamber, and the reverse;

a vial mixing device having a vial mixing rod which is positioned to selectively enter said chamber through the access opening from below to contact a supported vial and mix the contents by pulsation of the sample vial to increase the rate of transport of gaseous components from a liquid in said sample vial to said headspace, said rod contacting the bottom of the vial and being powered to pulse the vial vertically and mix the contents thereof;

a needle supported relative to the platen for extracting material from said headspace through said septum after the vial is heated and pulsed by operation of the rod;

said pulsed and heated vial being engageable with said needle by a movable member supported relative to the platen which drives said vial septum and needle into septum puncturing contact when the needle and chamber are aligned.

10. The device of claim 9, wherein each of said chambers is sized to slideably receive one of said sample vials and hold it in heat conductive relation to the platen.

11. The device of claim 10, wherein the vial mixing device in pulsating the vial causes the vial to move up and down within the chamber to maintain the vial in heat conductive relation to the platen.

12. The device of claim 9, wherein the platen comprises heat-conducting material.

13. The device of claim 12, wherein the platen comprises aluminum.

14. The device of claim 9, wherein a tip of said rod enters said chamber through the access opening from below to contact said supported vial.

15. The device of claim 9, wherein the electrically powered heater comprises a cartridge heater.

16. The device of claim 9, wherein said rod is selectively at least partially extendible into each of said plurality of side by side chambers.

17. A device for handling sample vials and heating and agitating the samples prior to withdrawing material from a headspace of each of the vials for analysis by gas chromatography, comprising:

a heated vial holder having a plurality of chambers each having an open end, and an opposite bottom vial retaining end with an aperture therein, each of the chambers being of a size to slidably receive one of the sample vials through the open end in a heat-conductive relationship to the vial holder and support the vial on the vial retaining end;

a needle for extracting the material from the headspace of the vials;

a mechanism for inserting and removing selected vials through the open ends into and from the respective vial holder chambers;

an insertion device to cause the needle to be selectively inserted in each of the vials carried in the chambers for extracting the material from the headspace; and a vial mixing device for agitating a vial in a chamber of the heated vial holder prior to extracting the material, the vial mixing device comprising an agitator acting through the aperture in the vial retaining end of the chamber and being operable to engage the vial in a resting position on the vial retaining end and cause agitation of the vial contents by reciprocally pulsing the vial while the vial is retained in the respective chamber of the vial holder.

18. The device of claim 17, wherein the vial mixing device in agitating the vial causes the vial to move up and down within the chamber to maintain the vial in heat conductive relation to the vial holder.

19. The device of claim 17, wherein the vial holder comprises heat-conducting material.

20. The device of claim 17, wherein the vial holder comprises aluminum.

21. The device of claim 17, wherein the agitator comprises a rod.

22. The device of claim 21, wherein a tip of the rod enters said chamber through the aperture from below to contact said vial.

23. The device of claim 17, wherein the heated vial holder comprises a cartridge heater.

24. The device of claim 17, wherein said agitator is selectively at least partially extendible into each of said plurality of chambers.

* * * * *